US005565138A

United States Patent [19]

Klaunzer et al.

[11] Patent Number: 5,565,138

[45] Date of Patent: Oct. 15, 1996

[54] BLEACH

[75] Inventors: Norman Klaunzer, Leverkusen; Ralf Wichmann, Bergisch Gladbach; Gustav Tappe, Leverkusen, all of Germany; Eltjo Boelema, B.C. Bathmen, Netherlands

[73] Assignee: Agfa AG, Germany

[21] Appl. No.: 329,990

[22] Filed: Oct. 27, 1994

[30] Foreign Application Priority Data

Nov. 5, 1993 [DE] Germany .......................... 43 37 846.3

[51] Int. Cl.[6] ............................ C01B 15/00; C07F 15/02; C07C 229/00; G03C 7/42

[52] U.S. Cl. ................................. 252/186.1; 252/186.33; 556/138; 556/148; 562/565; 430/393

[58] Field of Search ............................ 252/188.1, 186.1, 252/186.33; 556/138, 148; 562/565; 430/393

[56] References Cited

U.S. PATENT DOCUMENTS 3,107,260 10/1963 Knell ...................................... 260/439

FOREIGN PATENT DOCUMENTS 0293729 12/1988 European Pat. Off. .
0334317 9/1989 European Pat. Off. .
0534086 3/1993 European Pat. Off. .
0556782 8/1993 European Pat. Off. .
80/00624 4/1980 WIPO .

*Primary Examiner*—Shean C. Wu
*Attorney, Agent, or Firm*—Connolly and Hutz

[57] ABSTRACT

A bleach prepared from an iron (III) complex of a complexing agent of the formula I

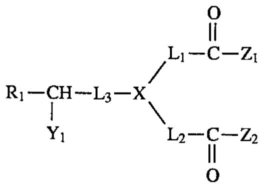

(I)

in which $L_1$, $L_2$ mean an optionally substituted alkylene group with 1 to 4 C atoms $L_3$ means an alkylene group with 1 to 4 C atoms, $Z_1$, $Z_2$ mean OH, $NH_2$, $NHR_2$, X means N, P=0, $SO_2H$ $Y_1$ means OH, $NH_2$, $NHR_3$, $NR_3R_4$, $SO_3H$, $PO_3H_2$, $NHCOR_5$, $R_1$, $R_2$, $R_3$, $R_4$ and $R_5$ mean optionally substituted alkyl or optionally substituted phenyl exhibits excellent bleaching action.

4 Claims, No Drawings

BLEACH

The invention relates to a bleach for photographic silver halide materials.

When processing photographic silver halide materials, it is necessary to bleach the silver produced on development, i.e., to oxidise it to silver ions, which, together with unexposed silver halide, are dissolved out of the material ("fixing") by means of a silver halide solvent, for example a thiosulphate. Bleaching and fixing may be performed in separate processing stages, but also together in a single stage (bleaching/fixing).

Good bleaches should have the following characteristics:

1. They should rapidly and completely bleach the exposed and developed material.
2. Bleaching should remain rapid and complete even at higher pH values.
3. They should not cause any fogging in the photographic material.
4. They should not reduce the cyan dye to the colourless leuco-compound.
5. They should be biodegradable.
6. They should not dissolve silver ions to form complexes.
7. They should preferably have an adequate bleaching action even in the absence of ammonium ions.

Requirements 1 to 4 are technical in nature, requirements 5 to 7 are of an ecological nature.

Iron (III) complexes of aminopolycarboxylic acids are customarily used as bleaches, for example complexes of ethylenediaminetetraacetic acid (EDTA), propylenediaminetetraacetic acid (PDTA), diethylenetriaminepentaacetic acid (DTPA) or nitrilodiaceticmononpropionic acid (ADA). None of these compounds fulfills all of the stated requirements.

The object of the invention was thus to provide bleaches with characteristics surpassing those of previously known bleaches.

It has now been found that this object may be achieved with novel iron (III) complexes.

The present invention thus provides a bleach prepared from an iron (III) complex of a complexing agent of the formula I

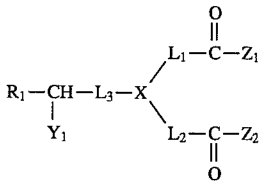

(I)

in which $L_1$, $L_2$ mean an optionally substituted alkylene group with 1 to 4 C atoms $L_3$ means an alkylene group with 1 to 4 C atoms, $Z_1$, $Z_2$ mean OH, $NH_2$, $NHR_2$, X means N, P═O, $SO_2H$ $Y_1$ means OH, $NH_2$, $NHR_3$, $NR_3R_4$, $SO_3H$, $PO_3H_2$, $NHCOR_5$, $R_1$, $R_2$, $R_3$, $R_4$ and $R_5$ mean optionally substituted alkyl or optionally substituted phenyl.

The compound may also be present as metal salts, in particular alkali metal salts.

The complexing agents of the bleaches according to the invention preferably correspond to the formula II

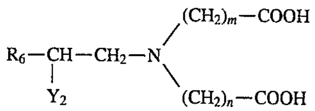

(II)

in which m and n mean a number from 1 to 4

$Y_2$ means OH or $NH_2$ and $R_6$ means an optionally substituted $CH_3$ group.

Suitable phenyl group substituents are $C_1$–$C_4$ alkyl, halogen and $C_1$–$C_4$ alkoxy.

Suitable alkyl group or $CH_3$ group substituents are phenyl, hydroxy and $C_1$–$C_4$ alkoxy.

Examples of complexing agents according to the invention are:

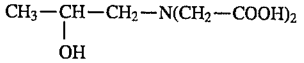

(1)

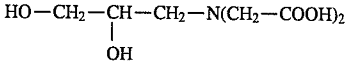

(2)

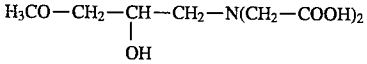

(3)

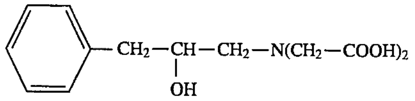

(4)

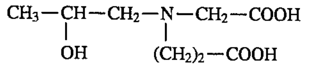

(5)

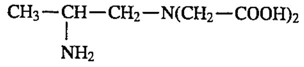

(6)

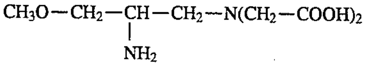

(7)

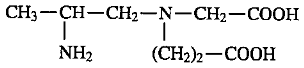

(8)

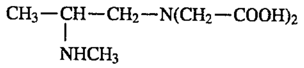

(9)

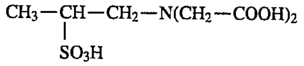

(10)

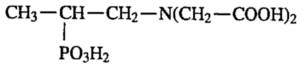

(11)

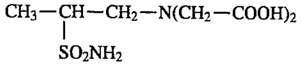

(12)

The invention also provides photographic processing baths with a bleaching action characterised by an effective content of iron (III) complexes with complexing agents of the formulae I or II.

The baths with bleaching action are bleaching baths or bleaching/fixing baths. Bleaching baths customarily additionally contain a rehalogenating agent, for example a soluble chloride, bromide or iodide, together with further customary constituents; bleaching/fixing baths customarily additionally contain a silver halide solvent, for example a thiosulphate.

Bleaching and bleaching/fixing baths customarily contain an excess of free complexing agent, which may amount to 1 to 120 mol. %, preferably 5 to 20 mol. %, related to the iron complex or iron complex salt.

The photographic processing baths with bleaching action according to the invention contain at least 20 mol.%, preferably at least 80 mol. % of the iron(III) complexes according to the invention. The remaining amount of at most 80 mol. %, preferably of at most 20 mol. %, may be iron (III) complexes with known complexing agents such as EDTA, PDTA, DTPA or ADA. Preferably, it is only the iron (III) complexes according to the invention which are used.

The iron complex is in particular used in the photographic processing baths with bleaching action according to the invention in a quantity of 0,005 to 1.2 mol/l.

The invention also provides a process for photographic processing having at least the stages (a) colour development and (b) bleaching and fixing or bleaching/fixing, characterised in that a processing bath with bleaching action according to the invention is used for bleaching or bleaching/fixing.

The processing process may be performed continuously with constant regeneration of the processing baths.

If bleaching baths with an elevated redox potential are used, entrainment of developer solution may bring about an increase in the minimum densities of the photographic material.

In the bleaching bath according to the invention, in order to prevent an increase in the minimum densities of the photographic material by entrainment of developer solution into the bleaching bath, substances may be added to the bleaching bath, rinsing bath or stop bath which scavenge the oxidation product of entrained developer solution, for example sulphite, citrazinic acid, white couplers or couplers which form unstable or readily water-soluble dyes.

The baths with bleaching action according to the invention are in particular suitable for colour photographic silver halide recording materials, the silver halide emulsions of which predominantly consist of AgBr, AgBrI, AgBrCl or AgCl. The colour photographic material preferably contains on a reflective or transparent support (for example paper coated on both sides with polyethylene or cellulose triacetate film) at least one blue-sensitive, at least one green-sensitive and at least one red-sensitive silver halide emulsion layer, which are associated in the stated order with at least one yellow coupler, at least one magenta coupler and at least one cyan coupler.

The bleaching performance (residual silver in the processed material) of the bleaching and bleaching/fixing baths listed in the examples was investigated. X-ray fluorescence analysis was used for this purpose.

EXAMPLE 1

A colour photographic recording material was produced by applying the following layers in the stated sequence to a film support of paper coated on both sides with polyethylene. The stated quantities relate to 1 $m^2$. The corresponding quantities of $AgNO_3$ are stated for the quantity of the silver halide applied.

Layer Structure

1st layer (substrate layer):

0.2 g gelatine

2nd layer (blue-sensitive layer):

Blue-sensitive silver halide emulsion (99.5 mol. % chloride, 0.5 mol. % bromide, average grain diameter 0.8 µm) prepared from 0.63 g $AgNO_3$ with 1.38 g gelatine 0.95 g yellow coupler Y 0.29 g tricresyl phosphate (TCP)

3rd layer (protective layer)

1.1 g gelatine 0.06 g 2,5-dioctylhydroquinone 0.06 g dibutyl phthalate (DBP)

4th layer (green-sensitive layer)

Green-sensitised silver halide emulsion (99.5 mol. % chloride, 0.5 mol. % bromide, average grain diameter 0.6 µm) prepared from 0.45 g $AgNO_3$ with 1.08 g gelatine 0.41 g magenta coupler M 0.08 g 2,5-dioctylhydroquinone 0.34 g DBP 0.04 g TCP 5th layer (UV protective layer)

1.15 g gelatine 0.6 g UV absorber of the formula

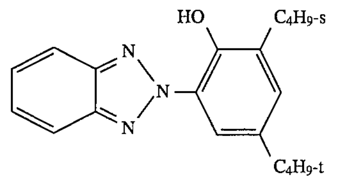

0. 045 g 2,5-dioctylhydroquinone 0.04 g TCP

6th layer (red-sensitive layer)

Red-sensitised silver halide emulsion (99.5 mol. % chloride, 0.5 mol. % bromide, average grain diameter 0.5 µm) prepared from 0.3 g $AgNO_3$ with 0.75 g gelatine 0.36 g cyan coupler C 0.36 g TCP 4th layer (UV protective layer)

0.35 g gelatine 0.15 g UV absorber as in 5th layer 0.2 g TCP

8th layer (protective layer)

0.9 g gelatine 0.3 9 hardener H of the following formula

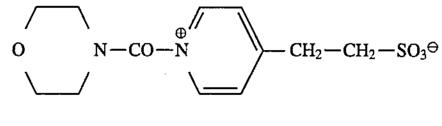

The components used are of the following formulae:

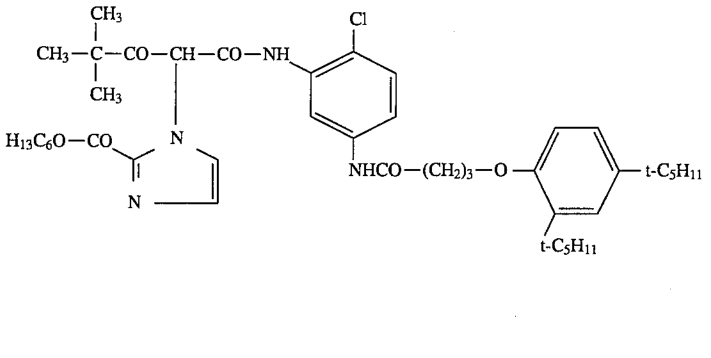

Y

-continued

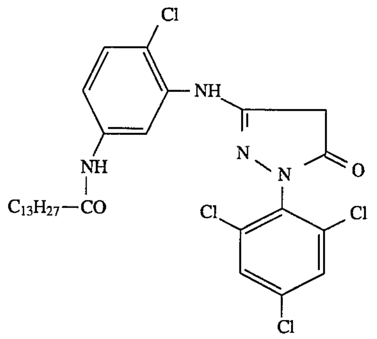

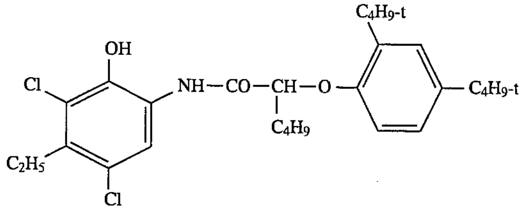

The above-described photographic recording material was exposed with a step wedge and processed as follows:

| | | |
|---|---|---|
| Development | 45 s | 35° C. |
| Rinsing | 22 s | <20° C. |
| Bleaching | 90 s | 35° C. |
| Rinsing | 45 s | 30° C. |
| Fixing | 45 s | 35° C. |
| Rinsing | 90 s | approx. 30° C. |
| Drying | | |

The individual processing baths were of the following composition:

| | |
|---|---|
| Developer: | |
| Water | 900 ml |
| Ethylenediaminetetraacetic acid (EDTA) | 2 g |
| Hydroxyethanediphosphonic acid (HEDP), 60 wt. % | 0.5 ml |
| Sodium chloride | 2 g |
| N,N-diethylhydroxylamine, 85 wt. % | 5 ml |
| 4-(N-ethyl-N-2-methanesulphonylamino-ethyl)-2-methylphenylenediamine sesqui-sulphate monohydrate (CD3), 50 wt. % | 8 ml |
| Potassium carbonate | 25 g |
| pH value adjusted to 10 with KOH or $H_2SO_4$. | |
| Make up to 1 liter with water. | |
| Bleaching bath | |
| Water | 800 ml |
| Iron (III) complex with complexing agent as per table 1 | 0.125 mol |
| Complexing agent as per table 1 | 0.013 mol |
| Ammonia, 25 wt. % | approx. 30 ml |
| Ammonium bromide | 0.51 mol |
| Make up to 1 liter with water | |
| pH | 4.0 |
| Fixing bath | |
| Water | 900 ml |
| Sodium sulphite | 10 g |
| Ammonium thiosulphate | 100 g |
| Adjust to pH 7 with ammonia or acetic acid. | |
| Make up to 1 liter with water. | |

TABLE 1

| Test | Complexing agent | Residual silver ($g/m^2$) | Comment |
|---|---|---|---|
| 1.1 | EDTA | 0.02 | Reference* |
| 1.2 | PDTA | 0.12 | Comparison |
| 1.3 | NTA | 0.22 | Comparison |
| 1.4 | ISDA | 0.30 | Comparison |
| 1.5 | HEIDA | 0.19 | Comparison |
| 1.6 | Compound 1 | 0.04 | Invention |

*Conditions currently most customarily used in practice; pH 6.
EDTA: Ethylenediaminetetraacetic acid
PDTA: Propylenediaminetetraacetic acid
NTA: Nitrilotriacetic acid
ISDA: Isoserinediacetic acid
HEIDA: Hydroxyethyleneiminodiacetic acid Table 1 shows that it is only the iron (III) complex of the compound according to the invention which achieves the bleaching action of the customary EDTA iron complex. EDTA is, however, very poorly biodegradable.

EXAMPLE 2

Tests were performed in a similar manner as in example 1, in which the cation in the bleaching bath was varied.

The only cation contained in all the bleaching solutions was the stated cation (with the exception of Fe (III)). The results are given in table 2.

TABLE 2

| Test | Complexing agent | Cation | Residual silver ($g/m^2$) | Comment |
|---|---|---|---|---|
| 2.1 | EDTA | $NH_4^{\oplus}$ | 0.02 | Reference* |
| 2.2 | EDTA | $Na^{\oplus}$ | 0.05 | Comparison |
| 2.3 | EDTA | $K^{\oplus}$ | 0.04 | Comparison |
| 2.4 | PDTA | $NH_4^{\oplus}$ | 0.12 | Comparison |
| 2.5 | PDTA | $K^{\oplus}$ | 0.20 | Comparison |
| 2.6 | Compound 1 | $NH_4^{\oplus}$ | 0.04 | Invention |
| 2.7 | Compound 1 | $Na^{\oplus}$ | 0.07 | Invention** |
| 2.8 | Compound 1 | $K^{\oplus}$ | 0.04 | Invention** |

*at pH 6 (see example 1)
**preferred range of the invention

The values show that excellent bleaching action is achieved with compound 1 according to the invention even if the ecologically questionable ammonium ions are avoided.

EXAMPLE 3

Example 1 was repeated, but the bleaching and fixing stages were replaced with bleaching/fixing. The rinsing stages before bleaching and between bleaching and fixing were omitted.

The bleaching/fixing bath was of the following composition:

| | |
|---|---|
| Water | 600 ml |
| Iron (III) complex with complexing agent as per table 3 | 0.25 mol |
| Complexing agent as per table 3 | 0.025 mol |
| $(NH_4)_2S_2O_3$ | 100 g |
| $Na_2SO_3$ | 25 g |
| Ammonia, 25 wt. % | approx. 50 ml |
| Water to make up to | 1000 ml |
| pH | 5.5 |

The results are shown in table 3:

TABLE 3

| Sample | Complexing agent | Residual silver ($g/m^2$) | Comment |
|---|---|---|---|
| 3.1 | EDTA | 0.025 | Reference*, no leuco-cyan |
| 3.2 | EDTA | 0.025 | Comparison, formation of leuco-cyan |
| 3.3 | Compound 1 | 0.010 | Invention, no leuco-cyan |

*at pH 6 (see example 1)

Compound 1 is superior to the customary EDTA. Even with only a slight drop in pH (from 6 to 5.5), there is a risk of leuco-cyan formation, i.e. loss of cyan density, with EDTA.

EXAMPLE 4

The following layers were applied in the stated sequence to a transparent cellulose triacetate film support.

The stated quantities relate to 1 $m^2$. The corresponding quantities of $AgNO_3$ are stated for the quantity of the silver halide applied.

All the silver halide emulsions were stabilised with 0.1 g of 4-hydroxy-6-methyl-1,3,3*a*,7-tetraazaindene per 100 g of $AgNO_3$.

| | |
|---|---|
| | 1st layer: (Anti-halo layer) |
| 0.2 g | black colloidal silver |
| 1.2 g | gelatine |
| 0.1 g | UV absorber UV 1 |
| 0.2 g | UV absorber UV 2 |
| 0.02 g | tricresyl phosphate |
| 0.03 g | dibutyl phthalate |
| | 2nd layer: (micrate interlayer) |
| 0.25 g | $AgNO_3$ of a micrate Ag (Br, I) emulsion: average grain $\phi = 0.07$ µm, 0.5 mol. % iodide |
| 1.0 g | gelatine |
| 0.05 g | coloured coupler RM 1 |
| 0.10 g | tricresyl phosphate |
| | 3rd layer: (low-sensitivity red-sensitised layer) |
| 2.2 g | $AgNO_3$, 4 mol. % iodide, average grain diameter 0.45 µm, red-sensitised |
| 2.0 g | gelatine |
| 0.6 g | colourless cyan coupler C1 emulsified in 0.5 g of tricresyl phosphate (TCP) |
| 50 mg | coloured cyan coupler RM 1 and |
| 30 mg | DIR coupler DIR 1 emulsified in 20 mg of TCP. |
| | 4th layer: (high-sensitivity red-sensitised layer) |
| 2.8 g | $AgNO_3$, 8.5 mol. % iodide, average grain diameter 0.8 µm, red-sensitised |
| 1.8 g | gelatine |
| 0.15 g | colourless cyan coupler C2 emulsified with 0.15 g of dibutyl phthalate (DBP) |
| | 5th layer: (interlayer) |
| 0.7 g | gelatine |
| 0.2 g | 2,5-diisoctylhydroquinone emulsified with 0.15 g of DBP |
| | 6th layer: (low-sensitivity green-sensitised layer) |
| 1.8 g | $AgNO_3$ of a spectrally green-sensitised Ag(Br, I) emulsion with 4.5 mol. % iodide and an average grain diameter of 0.4 µm, green-sensitised |

-continued

| | |
|---|---|
| 1.6 g | gelatine |
| 0.6 g | magenta coupler M1 (latex coupler) |
| 50 mg | mask coupler YM 1 emulsified with 50 mg of TCP |
| 30 mg | DIR coupler DIR 2 emulsified in 20 mg of DBP |
| 80 mg | DIR coupler DIR 3 emulsified in 60 mg of TCP |
| | 7th layer: (high-sensitivity green-sensitised layer) |
| 2.2 g | $AgNO_3$ with 7 mol. % iodide and an average grain diameter of 0.7 μm, green-sensitised |
| 1.4 g | gelatine |
| 0.15 g | magenta coupler M2 emulsified with 0.45 g of TCP |
| 30 mg | mask coupler as in 6th layer emulsified with 30 mg of TCP |
| | 8th layer: (interlayer) |
| 0.5 g | gelatine |
| 0.1 g | 2,5-diisooctylhydroquinone emulsified with 0.08 g of DBP |
| | 9th layer: (yellow filter layer) |
| 0.2 g | Ag (yellow colloidal silver sol) |
| 0.9 g | gelatine |
| 0.2 g | 2,5-diisooctylhydroquinone emulsified with 0.16 g of DBP |
| | 10th layer: (low-sensitivity blue-sensitive layer) |
| 0.6 g | $AgNO_3$, 4.9 mol. % iodide, average grain diameter 0.45 μm, blue-sensitised |
| 0.85 g | gelatine |
| 0.7 g | yellow coupler Y1 emulsified with 0.7 g of TCP |
| 0.5 g | DIR coupler DIR 3 emulsified with 0.5 g of TCP |
| | 11th layer: (high-sensitivity blue-sensitive layer) |
| 1.0 g | $AgNO_3$, 9.0 mol. % iodide, average grain diameter 0.9 μm, blue-sensitised |
| 0.85 g | gelatine |
| 0.3 g | yellow coupler as in 10th layer emulsified with 0.3 g of TCP |
| | 12th layer: (protective and hardening layer) |
| 0.5 g | $AgNO_3$ of a micrate Ag(Br, I) emulsion, average grain diameter 0.07 μm, 0.5 mol. % iodide |
| 1.2 g | gelatine |
| 0.4 g | hardener of the formula $(CH_2=CH-SO_2-CH_2-CONH-CH_2-)_2-$ |
| 1.0 g | formaldehyde scavenger of the formula |

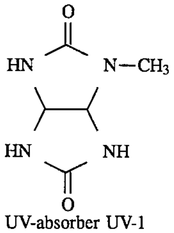

UV-absorber UV-1

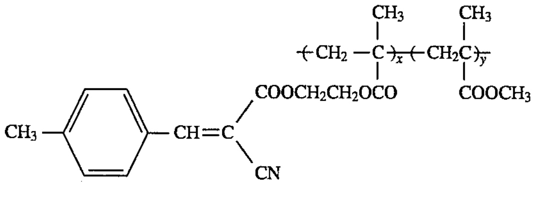

Weight ratio x:y = 7:3

UV-absorber UV-2

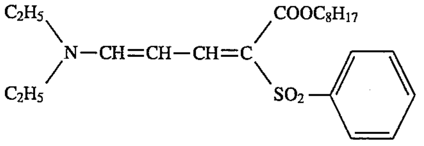

-continued
C1:
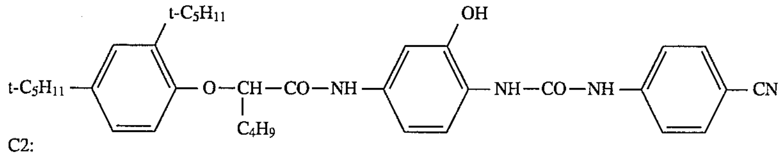
C2:
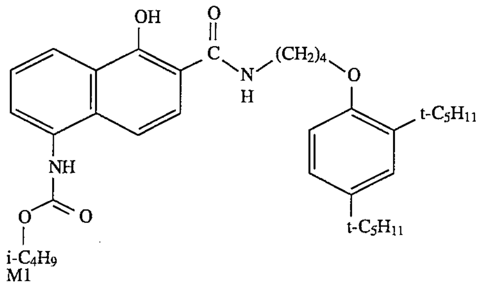
M1
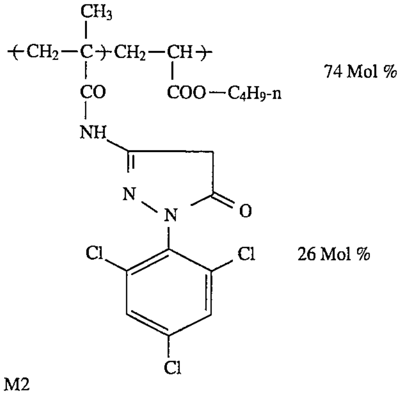
M2
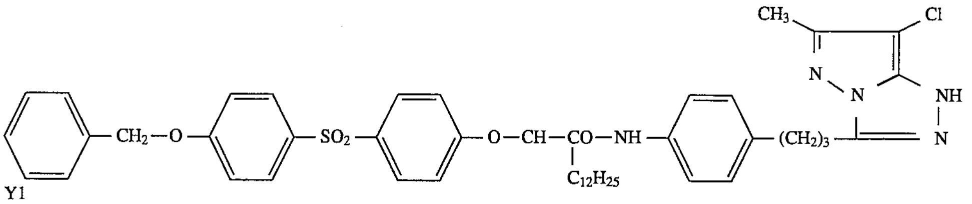
Y1
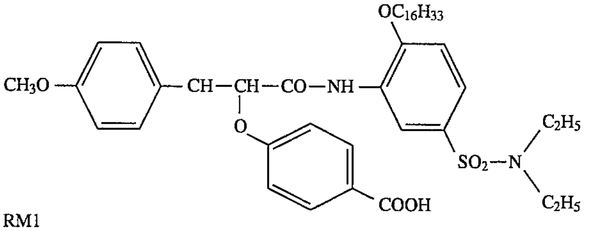
RM1
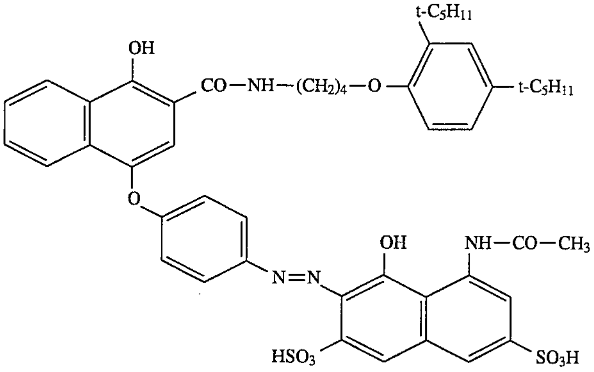

-continued

YM1

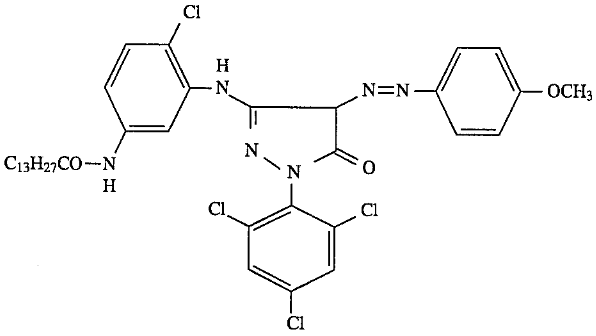

DIR1

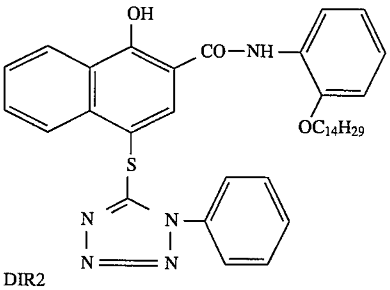

DIR2

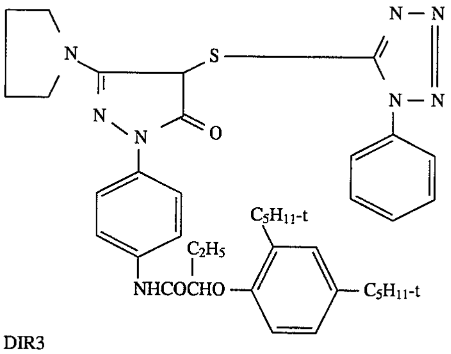

DIR3

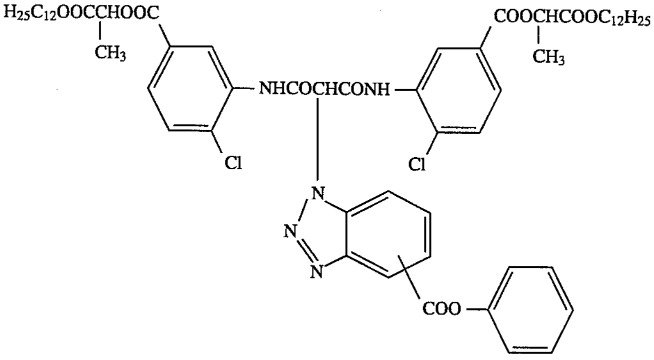

The above-described photographic recording material was exposed with a step wedge and processed as follows:

| | | |
|---|---|---|
| Developer | 3 min 15 s | 37.8° C. |
| Bleaching bath | 4 min 20 s | 38° C. |
| Rinsing | 1 min 5 s | 38° C. |
| Fixing bath | 4 min 20 s | 38° C. |
| Rinsing | 3 min 15 s | 38° C. |
| Finishing bath | 1 min 5 s | 38° C. |

The processing baths were of the following composition:

| | |
|---|---|
| Developer: | |
| Water | 800 ml |
| Potassium carbonate | 37.5 g |
| Sodium sulphite | 4.25 g |
| Potassium iodide | 1.2 mg |
| Sodium bromide | 1.3 g |
| Hydroxylamine sulphate | 2.0 g |
| Diethylenetriaminepentaacetic acid | 2.0 g |
| 4-(N-ethyl-N-β-hydroxyethylamino)-2- | |

-continued

| | |
|---|---|
| methylaniline sulphate | 4.75 g |
| Make up to 1 liter with water | |
| pH | 10.0 |
| Bleaching bath | |
| Water | 600 ml |
| Iron (III) complex with complexing agent as per table 4 | 0.27 mol |
| Free complexing agent | 0.03 mol |
| Ammonium bromide | 1.5 mol |
| Ammonium nitrate | 0.2 mol |
| Adjust to pH 4.2 with ammonia or acetic acid | |
| Make up to 1 liter with water | |
| Fixing bath | |
| Water | 800 ml |
| Ammonium thiosulphate solution (58 wt. %) | 162 ml |
| Ethylenediaminetetraacetic acid | 1.3 g |
| Sodium disulphite | 13 g |
| Sodium hydroxide | 2.4 g |
| Make up to 1 liter with water | |
| pH | 6.5 |
| Finishing bath | |
| Water | 800 ml |
| Formalin (37 wt. %) | 3 ml |
| Polyoxyethylene p-mononoylphenyl ether | 0.5 g |
| Make up to 1 liter with water | |

The residual silver results may be found in table 4 below. The colour image produced was equal to type.

TABLE 4

| Test | Complexing agent | Residual silver (g/m$^2$) | Bleaching fog[1)] ($\Delta D_{min}$ yellow) | Storage fog[2)] ($\Delta D_{min}$ yellow) | Comment |
|---|---|---|---|---|---|
| 4.1 | EDTA | 0.13 | — | 0.28 | Reference pH 6.0 |
| 4.2 | PDTA | 0.00 | 0.07 | 0.29 | Comparison |
| 4.3 | NTA | 0.21 | 0.00 | 0.20 | Comparison |
| 4.4 | ISDA | 1.10 | — | — | Comparison |
| 4.5 | HEIDA | 0.30 | — | — | Comparison |
| 4.6 | Compound 1 | 0.00 | 0.00 | 0.20 | Invention |

[1)]In comparison with test 1
[2)]After 14 days' storage at 80° C., 50% relative humidity With the exception of PDTA, neither NTA, ISDA or HEIDA, which are structurally very similar to compound 1, nor the standard bleach EDTA achieve the excellent bleaching action of the compound according to the invention. In contrast with PDTA, compound 1 produces no disruptive bleaching fog and lower fog than EDTA and PDTA. No fog values were determined in tests 4.4 and 4.5 due to the high residual silver contents.

EXAMPLE 5

Example 4 is repeated, wherein the pH value of the bleaching solution is varied as stated in table 5. Leuco-cyan formation was determined by determining the difference between the maximum cyan densities of the tests in the table and equivalent tests with 4 minutes' final bleaching. The results may be found in table 5.

TABLE 5

| | Complexing | Leuco-cyan ($\Delta D_{max}$ cyan) at pH | | | | |
|---|---|---|---|---|---|---|
| Test | agent | 6 | 5 | 4 | 3 | 2 |
| 5.1 | EDTA | 0.0 | 0.1 | 0.2 | — | — |
| 5.2 | PDTA | 0.0 | 0.0 | 0.14 | | — |
| 5.3 | Compound 1 | 0.0 | 0.0 | 0.0 | 0.0 | 0.03 |

— = not determined

The cyan dye is substantially more stable at lower pH against the iron complex with compound 1 according to the invention.

EXAMPLE 6

Similar tests to those in example 4 were performed in which the cation was varied in the bleaching bath (see example 2). The results are shown in table 6.

TABLE 6

| Test | Complexing agent | Cation | Residual silver (g/m$^2$) | Comment |
|---|---|---|---|---|
| 6.1 | EDTA | $NH_4$ | 0.13 | Reference* |
| 6.2 | EDTA | Na | 0.40 | Comparison |
| 6.3 | EDTA | K | 0.37 | Comparison |
| 6.4 | PDTA | $NH_4$ | 0.00 | Comparison |
| 6.5 | PDTA | K | 0.01 | Comparison |
| 6.6 | Compound 1 | $NH_4$ | 0.00 | Invention |
| 6.7 | Compound 1 | Na | 0.01 | Invention |
| 6.8 | Compound 1 | K | 0.00 | Invention |

*at pH 6.0

The ammonium-free complexing agents of the invention are equal to the ammonium-free PDTA bleaching bath, but have the advantage of better biodegradability. The same advantage applies in comparison with EDTA bleaching baths, the bleaching action of which is greatly surpassed by the bleaching complexes according to the invention.

EXAMPLE 7

Example 4 was repeated, but the bleaching bath and fixing bath were replaced with bleaching/fixing bath (6 min, 38° C.). Rinsing between bleaching and fixing was omitted.

| Bleaching/fixing bath | |
|---|---|
| Water | 600 ml |
| Iron (III) complex with complexing agent as per table 7 | 0.27 mol |
| Complexing agent as per table 7 | 0.03 mol |
| Thiosulphate | 0.80 mol |
| Sulphite | 0.02 mol |
| Adjust to pH 6 with alkali. | |
| Make up with water to | 1000 ml |

TABLE 7

| Test | Complexing agent | Cation | Residual silver ($g/m^2$) | Comment |
|---|---|---|---|---|
| 7.1 | EDTA | $NH_4^{\oplus}$ | 0.10 | Reference |
| 7.2 | EDTA | $Na^{\oplus}$ | 0.15 | Comparison |
| 7.3 | Compound 1 | $NH_4^{\oplus}$ | 0.01 | Invention |
| 7.4 | Compound 1 | $Na^{\oplus}$ | 0.03 | Invention* |
| 7.5 | Compound 1 | $K^{\oplus}$ | 0.02 | Invention* |

*preferred range.

The iron complex of compound 1 according to the invention exhibits excellent bleaching action even in the absence of the ecologically undesirable ammonium ions.

We claim:

1. Bleach prepared from an iron (III) complex of a complexing agent of the formula 1

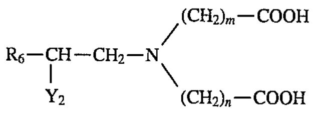

(I)

wherein m and n are the same or different and are a number from 1 to 4, $Y_2$ is OH or $NH_2$ and $R_6$ is an unsubstituted $CH_3$ group or a $CH_3$ group substituted by hydroxy, phenyl or $C_1$–$C_4$-alkoxy.

2. Bleach according to claim 1 prepared from an iron (III) complex of a complexing agent of the formula

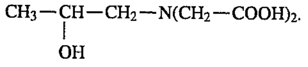

3. Photographic processing bath with bleaching action characterised by an effective content of at least one iron (III) complex according to claim 1.

4. Process for photographic processing having at least the stages (a) color development and (b) bleaching and fixing or bleaching/fixing, characterised in that a processing bath with bleaching action according to claim 3 is used for bleaching or bleaching/fixing.

* * * * *